United States Patent [19]

Dieterich

[11] 4,279,832
[45] Jul. 21, 1981

[54] PROCESS FOR THE PRODUCTION OF ISOCYANATOARYL SULFONIC ACIDS

[75] Inventor: Dieter Dieterich, Leverkusen, Fed. Rep. of Germany

[73] Assignee: Bayer Aktiengesellschaft, Leverkusen, Fed. Rep. of Germany

[21] Appl. No.: 171,562

[22] Filed: Jul. 23, 1980

[30] Foreign Application Priority Data

Aug. 8, 1979 [DE] Fed. Rep. of Germany ....... 2932094

[51] Int. Cl.$^3$ .................. C07C 118/00; C07C 143/24; C07D 229/00
[52] U.S. Cl. .......................... 260/453 P; 260/239 A; 260/453 PH; 260/453 AR; 260/453 AM
[58] Field of Search ..... 260/453 P, 453 PH, 453 AR, 260/453 AM, 239 AL

[56] References Cited

U.S. PATENT DOCUMENTS

| | | | |
|---|---|---|---|
| 3,826,769 | 7/1974 | Carlson | 260/29.2 TN |
| 3,959,329 | 5/1976 | Dieterich et al. | 260/453 AR |
| 4,119,658 | 10/1978 | Dieterich | 260/453 AR |
| 4,144,267 | 3/1979 | Dieterich et al. | 260/505 R |
| 4,176,118 | 11/1979 | Petinaux et al. | 260/239 A |

FOREIGN PATENT DOCUMENTS 1278426  6/1972  United Kingdom .
1383184  2/1975  United Kingdom .

*Primary Examiner*—Dolph H. Torrence
*Attorney, Agent, or Firm*—Gene Harsh; Joseph C. Gil

[57] ABSTRACT

The present invention relates to a new process for the production of isocyanatoaryl sulfonic acids which are optionally present, at least partly, as salts of an inorganic or organic base, by sulfonation of the corresponding carbamic acid chlorides, conversion of the carbamic acid chloride groups into isocyanate groups and optionally, subsequent neutralization of at least some of the sulfonic acid groups present.

7 Claims, No Drawings

PROCESS FOR THE PRODUCTION OF ISOCYANATOARYL SULFONIC ACIDS

FIELD OF THE INVENTION

The present invention relates to a new process for the production of isocyanatoaryl sulfonic acids which are optionally present, at least partly, as salts of an inorganic or organic base, by sulfonation of the corresponding carbamic acid chlorides, conversion of the carbamic acid chloride groups into isocyanate groups and, optionally, subsequent neutralization of at least some of the sulfonic acid groups present.

Isocyanatoaryl sulfonic acids (that is, aromatic isocyanates which contain sulfonic acid groups) are known. These known compounds are either distinct monosulfonic acids or polysulfonic acids (cf. German Offenlegungsschriften Nos. 1,939,911; 2,524,476 and 2,615,876) or polyisocyanate mixtures. These polyisocyanate mixtures often only proportionately contain isocyanatoaryl sulfonic acids (German Offenlegungsschriften Nos. 2,227,111; 2,359,614 and 2,359,615). Until now, these products were produced by the sulfonation of corresponding isocyanates, preferably with sulfur trioxide. The isocyanate groups in these sulfonation products are often present in the form of their dimers (uretdiones).

It has been found that the production of isocyanatoaryl sulfonic acids by sulfonation of the corresponding carbamic acid chlorides with simultaneous or subsequent hydrogen chloride evolution gives particularly good yields. Additionally, the purification of the corresponding aryl isocyanates is not necessary. This is a substantial simplification of the known processes for the production of isocyanatoaryl sulfonic acids by the sulfonation of the corresponding isocyanates. By following the principle of the instant invention, the production of aryl isocyanates by phosgenation of the corresponding aryl amines can be combined with the sulfonation reaction. Particularly surprising was the observation that hydrogen chloride evolution from the sulfonated carbamic acid chlorides takes place more smoothly and simply than the evolution of hydrogen chloride from the corresponding unsulfonated carbamic acid chlorides formed as intermediate products in the phosgenation of the corresponding amines. The isocyanatoaryl sulfonic acids which can be obtained by the instant invention can be converted into the corresponding derivatives, which are present at least partly in the form of salts, by the simple neutralization of at least some of the sulfonic acid groups present.

DESCRIPTION OF THE INVENTION

The instant invention relates to a process for the production of isocyanatoaryl sulfonic acids optionally present at least partly as salts of an inorganic or organic base, characterized in that aromatic carbamic acid chlorides are reacted with sulfur trioxide or chlorosulfonic acid at a temperature of from $-10°$ C. to $140°$ C., the carbamic acid chloride groups present are simultaneously or subsequently converted into isocyanate groups by a heat treatment at a temperature of from $40°$ C. to $180°$ C. with the evolution of hydrogen chloride and finally, optionally, at least some of the sulfonic acid groups present are converted into sulfonate groups by neutralization with an inorganic or organic base.

The isocyanate groups in the products of the instant invention are often present, at least partly, in a dimerized form, i.e. as uretdione groups. Particularly in the sulfonation of aryl-monocarbamic acid chlorides, the sulfonic acid groups introduced by the sulfonation reaction can also be present, at least partly, in the form of the corresponding anhydride groups. The term "isocyanatoaryl sulfonic acids" thus includes, within the context of the instant invention, the corresponding compounds having free sulfonic acid groups and free isocyanate groups as well as the corresponding compounds having uretdione groups and sulfonic acid anhydride groups. Even in the products of the process which are present at least partly as salts, some of the isocyanate groups can be present in a dimerized form as uretdione groups.

The starting materials for the instant process are any aryl carbamic acid chlorides (that is, any aromatic compounds having at least one aromatically bound carbamic acid chloride group and aromatic compounds optionally having other substitutes which are inert to the sulfonation reaction). The starting materials for the instant process are preferably compounds which contain from 1 to 4 aromatic rings and from 1 to 4 aromatically bound carbamic acid chloride groups and which also satisfy the above conditions. Preferred starting materials for the instant process include carbamic acid chlorides according to the following formula:

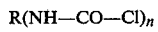

wherein

R represents an n-valent aromatic hydrocarbon radical optionally having methyl substituted and/or methylene bridges, and containing a total of from 6 to 30, preferably from 7 to 15, carbon atoms, and n represents an integer of from 2 to 4, preferably 2.

Mixtures of carbamic acid chlorides of this kind can also be used. The preferred carbamic acid chlorides of the above-mentioned formula have at least one and at the most two carbamic acid chloride groups on each aromatic ring.

Examples of suitable monocarbamic acid chlorides include phenyl, p-toluyl, p-chlorophenyl, p-nitrophenyl, p-methoxy phenyl, m-chlorophenyl, m-chloromethylphenyl or p-chloromethylphenyl carbamic acid chloride. Examples of suitable bis-carbamic acid chlorides include benzene-1,4-bis carbamic acid chloride, toluene-2,4-bis-carbamic acid chloride, naphthalene-1,5-bis-carbamic acid chloride, diphenylmethane-4,4'- or 2,4-bis-carbamic acid chloride, stilbene-4,4'-bis-carbamic acid chloride, 3,3'-dichlorodiphenylmethane-4,4'-bis-carbamic acid chloride, diphenylpropane-4,4'-bis-carbamic acid chloride, diphenylether-4,4'-bis-carbamic acid chloride, diphenylsulfide-4,4'-bis-carbamic acid chloride or diphenylsulfone-4,4'-bis-carbamic acid chloride. Examples of higher functional carbamic acid chlorides (n=3 or 4) which are particularly suitable for the instant process include the carbamic acid chlorides resulting from the reaction of three nuclear or four nuclear aniline/formaldehyde condensates, i.e. the higher homologues of diamino-diphenylmethane isomers with phosgene. Examples of particularly preferred carbamic acid chlorides which are suitable for the instant process include toluene-2,4-bis-carbamic acid chloride, toluene-2,6-bis-carbamic acid chloride or mixtures of these isomers. Also preferred are, for example, diphenylmethane-4,4'-bis-carbamic acid chloride, diphenylmethane-2,4'-bis-carbamic acid chloride, mixtures of these isomers, as well as mixtures of these last-mentioned isomers with the carbamic acid chlorides which were mentioned above and which are higher than difunctional, for example, as are obtained from the reaction of aniline/formaldehyde condensates with phosgene.

In carrying out the instant process, chlorosulfonic acid or sulfur trioxide is used as a sulfonating agent. Sulfur trioxide can be used as a fluid in the form of a solution or as a gas optionally diluted in an inert gas, for example in nitrogen. Sulfur trioxide may also be used in the form of an addition compound to suitable organic compounds. A suitable solvent for sulfur trioxide is, for example, concentrated sulfonic acid (fuming sulfuric acid being the sulfonating agent). Addition compounds of sulfur trioxide with suitable organic compounds include, for example, pyridine-$SO_3$, dioxane-$SO_3$, tetrahydrofuran-$SO_3$, ether-$SO_3$ or dimethyl formamide-$SO_3$. Sulfonation is preferably carried out with gaseous sulfur trioxide diluted in a nitrogen stream, with fuming sulfuric acid or with chloro-sulfonic acid.

The sulfonation reaction is preferably carried out in the presence of solvents which are chemically inert to $SO_3$ and NCO-groups under the reaction conditions used. An example of such solvents include dichloroethane, tetrachloroethane, methylene chloride, chloroform, nitromethane, tetrahydrofuran, phosphorus oxychloride, dioxane and nitrobenzene. In special cases, particularly in the case of partial sulfonation, chlorobenzene and o-dichlorobenzene can also be used.

The amount of the sulfonating agent which is used amounts to from 0.01 to 6 mols per mol of aromatic carbamic acid chloride. If only partial sulfonation is being carried out, then the amount of the sulfonating agent per mol of the carbamic acid chloride which is used amounts to from 0.01 to 0.95 mol and preferably from 0.05 to 0.4 mol. In order to get the best results when carrying out monosulfonation, from 0.95 to 1.3 mols, preferably from 1.0 to 1.1 mols of the sulfonating agent are used. In order to carry out polysulfonation, from 1.3 to 6.0 mols, preferably from 2.0 to 4.0 mols of the sulfonating agent are required. In this case, quantities of more than 2.0 mols are in practice only employed where carbamic acid chlorides having two or three aromatic rings are used.

Generally, sulfonation is carried out at a temperature of between $-10°$ C. and $140°$ C., preferably between $0°$ C. and $80°$ C. The sulfonating agent can either be added gradually to the solution or alternatively to the suspension of the carbamic acid chloride. Alternatively, the carbamic acid chloride can be allowed to run into the sulfonating agent. In solution, the sulfonation reaction takes place almost instantaneously whereas, in suspension, it usually takes place within a few minutes. In the combination which is particularly preferred (the production of polyisocyanates by phosgenation of the corresponding amines followed by the sulfonation reaction), the sulfonation takes place by the addition of the sulfonating agent at a temperature within the disclosed ranges to the carbamic acid chloride (resulting from the phosgenation of the corresponding amines) any time from immediately after mixing the amine with the phosgene to immediately before the conversion of the carbamic acid chloride intermediates into the corresponding isocyanates by the thermal evolution of hydrogen chloride.

After the sulfonation reaction, elimination of hydrogen halide from the sulfonated carbamic acid chloride to form the sulfonated isocyanate is carried out in the conventional manner for the production of isocyanates. That is, the reaction mixture is warmed to a temperature of from $40°$ C. to $180°$ C. and, in order to accelerate the process, a stream of inert gas (nitrogen, carbon dioxide) is passed through the reaction mixture.

The elimination of hydrogen halide is facilitated by the presence of the sulfonic acid groups. The presence of the sulfonic acid groups allows the gas evolution to take place at a lower temperature than when unsubstituted carbamic acid chlorides alone are used. If polysulfonation is carried out, the evolution of hydrogen chloride can even take place at room temperature during the sulfonation process.

The reaction products of monosulfonation or polysulfonation are solid products which are insoluble in most solvents and which can be separated from the solvents preferably by decanting, filtration or centrifugation. In most cases, suitable uretdiones are those which, because of their extreme sensitivity to moisture, can be processed further when they are still moist. If only partial sulfonation is carried out, then the isocyanatoaryl sulfonic acid either remains dissolved or when the solvent is distilled off, passes into solution. Then fluid, modified isocyanates are obtained, as they are described in German Offenlegungsschriften Nos. 2,227,111 and 2,359,614.

The isocyanate groups in the products of the instant process are often present, at least partly, in a dimerized form. The sulfonic acid groups—particularly when using monofunctional carbamic acid chlorides as a starting material—are often present, at least partly, in the form of sulfonic acid anhydride groups. The free sulfonic acid groups which are present in the products of the instant process can be completely or partially converted into the corresponding sulfonate groups by reaction with bases, particularly with tertiary amines. Suitable tertiary amines include, for example, trimethyl amine, triethyl amine, tributyl amine, dimethyl aniline or pyridine. Conversion of the acids into the corresponding salts takes place, for example, by suspending the acids in a nonsolvent, for example tetrachloroethane, or by dissolving the acids in a solvent, for example acetone, and the addition of the tertiary amine used for the production of the salts. These salts can also, however, be produced, for example, by gasing the pulverous acids with gaseous tertiary amines. The production of salts of the products of the instant process with inorganic bases takes place, for example, by the reaction of solutions of the acids in, for example, acetone with alkali metal dispersions or alkali metal hydride dispersions, especially dispersions of sodium, sodium hydride or potassium in, for example, toluene.

The preferred products of the instant process are characterized as containing isocyanate groups, optionally present in a dimerized form, of from 10 to 42% by weight and by a content of sulfur, present in the form of sulfonic acid groups, sulfonate groups and/or sulfonic acid anhydride groups, of from 0.5 to 20% by weight.

The products of the instant process are very useful compounds. More particularly they are hydrophilic non-toxic isocyanates suitable as starting material for making (poly)urethanes and (poly)ureas. From partly sulfonated polyisocyanates inorganic/organic foams and compositions can be made which are suitable as construction material. Preferred coreactants for this type of polyisocyanates are aqueous solutions of alkali metal silicates and aqueous suspensions or slurries of inorganic particulate material, e.g. calcium carbonate, hydraulic cement, silica, sand and the like.

Moreover the products of the instant process are useful intermediates for the production of sulfonic ester isocyanates and isocyanatoaryl-sulfochlorides. The products of the instant process in admixture with epoxides, oxetanes and optionally polyols lead to polyurethanes with sulfonic ester groups which are disclosed in German Offenlegungsschrift No. 2,735,047 which corresponds to U.S. Application Ser. No. 929,616 filed on July 31, 1978, U.S. Pat. No. 4,237,250.

The following Examples serve to illustrate the process of the invention without restricting it in any way. In the Examples, all quantities quoted represent parts by weight or percent by weight, unless otherwise indicated.

EXAMPLES

Example 1

123.5 g (0.5 mol) of toluene-bis-carbamic acid chloride (80% 2,4-isomer, 20% 2,6-isomer) are suspended in 500 ml of 1,2-dichloroethane. Into the suspension are introduced 42 g (0.525 mol) of sulfur trioxide at a temperature of from 2° to 10° C. This is subsequently slowly warmed with stirring and HCl evolution takes place once the temperature reaches 50° C. When the temperature reaches 85° C., the HCl evolution is virtually finished. Nitrogen is passed through the suspension until the waste gas is free from HCl. It is then filtered off, washed with dichloroethane and dried. 92 g of a powder is obtained, the IR-spectrum of which corresponds to that of the product obtained according to Example 1 of German Offenlegungsschrift No. 2,640,103. This is the uretdione of tolylene diisocyanate-5-sulfonic acid.

Example 2

The same product as described in Example 1 is obtained when 0.5 mol of an isomer mixture consisting of 2,4-diamino toluene and 2,6-diamino toluene (weight ratio=80:20) and 2 mols of phosgene are mixed thoroughly in 500 ml of 1,2-dichloroethane at 0° C. The corresponding bis-carbamic acid chloride is obtained by passing phosgene through, warming at 50° C.-70° C., sulfonating with sulfur trioxide or chlorosulfonic acid and then heating to 85° C. and removing hydrogen chloride by passing nitrogen through.

Example 3

19.8 g (0.1 mol) of 4,4'-diamino-diphenylmethane in 50 ml of 1,2-dichloroethane are stirred intensively into a solution (cooled to −10° C.) of 40 g (0.4 mol) of phosgene in 100 ml of 1,2-dichloroethane, wherein diphenylmethane-bis-carbamic acid chloride is obtained. 12 g (0.1 mol) of chlorosulfonic acid are subsequently added. While passing nitrogen through, the suspension is heated until boiling, whereby the majority of the hydrogen chloride is evolved. After adding 50 ml of 1,2-dichlorobenzene and distilling off 1,2-dichloroethane by a short period of heating at 140° C., the residue is removed.

The product of the reaction corresponds to that obtained according to Example 1 of German Offenlegungsschrift No. 2,524,476. This is the uretdione of 4,4'-diisocyanato-diphenylmethane-3-sulfonic acid.

Example 4

100 g of a polyamine mixture of the diphenylmethane series, which is produced by an acidic catalyzed aniline/formaldehyde condensation and which contains 44% of diamino-diphenylmethane isomers, 24% of three nuclear triamines and 32% of higher nuclear homologues, are dissolved in 200 ml of chlorobenzene. This solution is then stirred intensively into a solution, which is cooled to 5° C., of 200 g of phosgene in 500 ml of chlorobenzene, thus forming the corresponding carbamic acid chloride mixture. Subsequently, 4 g of sulfur trioxide are introduced. The reaction mixture is heated to boiling with more phosgene being passed through and, subsequently, nitrogen is passed through until no more hydrogen chloride evolves. After distilling off the chlorobenzene, a homogeneous, fluid, sulfonated polyisocyanate is obtained. Viscosity: 830 cP; S-content: 1.3%; NCO-content: 31.2%.

What is claimed is:
1. A process for the production of isocyanatoaryl sulfonic acids comprising:
   (a) reacting a mixture of reaction components comprising:
      (i) aromatic carbamic acid chlorides,
      (ii) sulfur trioxide or chlorosulfonic acid, at a temperature of from −10° C. to 140° C. to produce sulfonic acids with carbamic acid chloride groups;
   (b) converting said carbamic acid chloride groups into isocyanate groups by heating to a temperature of 40° C. to 180° C. with the evolution of hydrogen chloride; and optionally,
   (c) neutralizing at least some of the sulfonic acid groups present with an inorganic or organic base forming sulfonate groups.
2. A process as claimed in claim 1 wherein component (i) is a carbamic acid chloride of the formula:

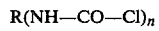

R(NH—CO—Cl)$_n$ wherein
R represents an n-valent aromatic hydrocarbon radical having from 6 to 30, preferably 7 to 15, carbon atoms, optionally methyl substituted or containing methylene bridges,
n represents an integer of from 2 to 4, preferably 2, or mixtures thereof.
3. A process as claimed in claim 1 wherein component (i) is selected from the group consisting of toluene-2,4-bis-carbamic acid chloride, toluene-2,6-bis-carbamic acid chloride, mixtures of these isomers, diphenylmethane-4,4'-bis-carbamic acid chloride, diphenylmethane-2,4'-bis-carbamic acid chloride or mixtures of these isomers, and mixtures thereof.
4. A process as claimed in claim 1 wherein component (ii) is sulfur trioxide or fuming sulfuric acid.
5. A process as claimed in claim 1 wherein component (ii) is gaseous sulfur trioxide diluted in nitrogen gas.
6. A process as claimed in claim 1 wherein component (ii) is used in an amount of from 0.01 to 6 mols per mol of component (i).
7. A process as claimed in claim 1 wherein step (a) is carried out at a temperature of from 0° C. to 80° C.

* * * * *